United States Patent
Kim et al.

(10) Patent No.: US 12,371,669 B2
(45) Date of Patent: Jul. 29, 2025

(54) KIDNEY ORGANOIDS AND METHOD FOR PRODUCING THE SAME

(71) Applicants: POSTECH Research and Business Development Foundation, Pohang-si (KR); UNIST(ULSAN NATIONAL INSTITUTE OF SCIENCE AND TECHNOLOGY), Ulsan (KR)

(72) Inventors: Dong Sung Kim, Pohang-si (KR); Tae Eun Park, Ulsan (KR); Hyeon Ji Lim, Ulsan (KR); Do Hui Kim, Incheon (KR)

(73) Assignees: POSTECH RESEARCH AND BUSINESS DEVELOPMENT FOUNDATION, Pohang-si (KR); UNIST(ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 0 days.

(21) Appl. No.: 17/980,820

(22) Filed: Nov. 4, 2022

(65) Prior Publication Data

US 2023/0142476 A1 May 11, 2023

(30) Foreign Application Priority Data

Nov. 9, 2021 (KR) .................. 10-2021-0153107
Sep. 23, 2022 (KR) .................. 10-2022-0120733

(51) Int. Cl.
*C12N 5/071* (2010.01)

(52) U.S. Cl.
CPC ........ *C12N 5/0697* (2013.01); *C12N 2500/02* (2013.01); *C12N 2501/119* (2013.01); *C12N 2501/16* (2013.01); *C12N 2506/45* (2013.01); *C12N 2513/00* (2013.01)

(58) Field of Classification Search
None
See application file for complete search history.

(56) References Cited

U.S. PATENT DOCUMENTS

| | | |
|---|---|---|
| 10,369,254 B2 | 8/2019 | Yanagawa et al. |
| 2018/0258404 A1* | 9/2018 | Bonventre ........... C12N 5/0686 |
| 2020/0248147 A1* | 8/2020 | Homan ............... A61K 35/22 |
| 2022/0073852 A1* | 3/2022 | Lee ................... C12M 25/04 |

FOREIGN PATENT DOCUMENTS

| | | | | |
|---|---|---|---|---|
| JP | 2015-123028 | 7/2015 | | |
| JP | 2017-537655 | 12/2017 | | |
| JP | 2018-102285 | 7/2018 | | |
| JP | 2018-527007 | 9/2018 | | |
| KR | 20200010279 | 1/2020 | | |
| KR | 10-2020-0081853 | 7/2020 | | |
| WO | 2016/094948 | 6/2016 | | |
| WO | WO-2016094948 A1 * | 6/2016 | ........... | C12N 5/0686 |
| WO | 2020/019023 | 1/2020 | | |
| WO | WO-2020138581 A1 * | 7/2020 | ............. | B29C 51/08 |

OTHER PUBLICATIONS

Futrega et al. The microwell-mesh: A novel device and protocol for the high throughput manufacturing of cartilage microtissues (2015) Biomaterials, 62, pp. 1-12. (Year: 2015).*
Gupta et al. Microfluidics-based 3D cell culture models: Utility in novel drug discovery and delivery research (2016) Bioengineering & Translational Medicine, 1, pp. 63-81. (Year: 2016).*
Minoru Takasato et al., "Generation of kidney organoids from human pluripotent stem cells", Nature Protocols vol. 11, pp. 1681-1692, Aug. 18, 2016.
EPO, Search Report of EP 22205804.2 dated Feb. 23, 2023.
Kohei Uchimura et al., "Human Pluripotent Stem Cell-Derived Kidney Organoids with Improved Collecting Duct Maturation and Injury Modeling", Cell Reports 33, 108514, Dec. 15, 2020, https://doi.org/10.1016/j.celrep.2020.108514.
KIPO, Office Action of KR 10-2021-0153107 dated Jun. 21, 2024.
Ramírez-Bergeron, Diana L., et al. "Hypoxia affects mesoderm and enhances hemangioblast specification during early development." Development 131 (Sep. 2004): 4623-4634. doi: 10.1242/dev.01310.
JPO, Office Action of the corresponding Japanese Patent Application No. 2022-178961 dated Nov. 28, 2023.

* cited by examiner

*Primary Examiner* — Peter Paras, Jr.
*Assistant Examiner* — Maytee Marie Contes De Jesus
(74) *Attorney, Agent, or Firm* — LEX IP MEISTER, PLLC

(57) ABSTRACT

Disclosed is a method for producing kidney organoids including steps of: (1) differentiating stem cells into metanephric mesenchyme cells; (2) forming metanephric mesenchyme cell aggregates by culturing the metanephric mesenchyme cells; and (3) differentiating the metanephric mesenchyme cell aggregates into kidney organoids.

4 Claims, 16 Drawing Sheets

KIDNEY ORGANOIDS AND METHOD FOR PRODUCING THE SAME

BACKGROUND

1. Technical Field

The present disclosure relates to kidney organoids and a method for producing the same, and more particularly, to a method of forming kidney organoids having a more improved nephron structure by applying permeable porous wells and a new protocol.

2. Related Art

Differentiation of pluripotent stem cells (PSCs), including embryonic stem cells (ESCs) and induced pluripotent stem cells (iPSCs), permitted the generation of organoid models of various tissues, including kidneys.

Kidney organoids are three-dimensional cell aggregates generated by mimicking the developmental process of kidneys, are composed of various kidney cells, exhibit a structure similar to that of the kidney, and thus show potential as in vitro kidney models for the evaluation of nephrotoxicity of drugs and studies on therapeutic agents for kidney diseases. Accordingly, many studies have been conducted for the generation of kidney organoids, and various methods for generating kidney organoids have been proposed.

In general, three-dimensional kidney organoids are generated using well-type platforms such as well plates and microwell arrays that can form three-dimensional aggregates from cells. However, in the case of conventional impermeable wells, the supply of nutrients and growth factors and the removal of metabolites are not smooth, and thus the viability of kidney organoids may be lowered, causing immaturity.

Meanwhile, with recent advances in the field of stem cells, several different protocols for generating kidney organoids from human pluripotent stem cells (hPSCs) have been established. hPSC-derived kidney organoids have segmented structures with podocytes, proximal tubule epithelial cells and distal tubule epithelial cells in nephron-like arrangements. Comparative analysis of hPSC-derived kidney organoids in vitro and kidney tissue in vivo showed that kidney organoids recapitulate human kidney development. However, limited vascularization and immaturity of nephron-like structures have been still remain to be overcome.

PRIOR ART DOCUMENTS

Patent Documents (Patent Document 0001) KR 10-2020-0010279

SUMMARY

Accordingly, one aspect of the present disclosure is intended to provide a method of producing kidney organoids having a more improved nephron structure by applying permeable porous wells and a novel protocol.

According to one aspect of the present disclosure, there is provided a method for producing kidney organoids including steps of: (1) differentiating stem cells into metanephric mesenchyme cells; (2) forming metanephric mesenchyme cell aggregates by culturing the metanephric mesenchyme cells; and (3) differentiating the metanephric mesenchyme cell aggregates into kidney organoids.

According to another aspect of the present disclosure, there may be provided a cell aggregate including metanephric mesenchyme cells differentiated from stem cells under a hypoxic condition, wherein the expression level of Brachyury (T) in the cell aggregate is higher than that in a cell aggregate including metanephric mesenchyme cells differentiated from stem cells under a normoxic condition, the hypoxic condition is a condition with an oxygen concentration of more than 1% to less than 10%, and the normoxic condition is a condition with an oxygen concentration of 10% or more.

According to still another aspect of the present disclosure, there may be provided a kidney organoid differentiated from a metanephric mesenchyme cell aggregate formed under a hypoxic condition, wherein the expression levels of mRNA corresponding to proximal tubules, mRNA corresponding to Henle loops, and mRNA corresponding to distal tubules in the kidney organoid are higher than those in a kidney organoid differentiated from a metanephric mesenchyme cell aggregate formed under a normoxic condition, the hypoxic condition is a condition with an oxygen concentration of more than 1% to less than 10%, and the normoxic condition is a condition with an oxygen concentration of 10% or more.

According to yet another aspect of the present disclosure, there may be provided a kidney organoid differentiated from a metanephric mesenchyme cell aggregate formed under a hypoxic condition, wherein the kidney organoid is connected to an adjacent kidney organoid by a tubular structure, and the hypoxic condition is a condition with an oxygen concentration of more than 1% to less than 10%.

According to still yet another aspect of the present disclosure, there may be provided a kidney organoid differentiated from a metanephric mesenchyme cell aggregate formed under a hypoxic condition, wherein the expression level of at least one of mRNA corresponding to principal cells constituting a collecting duct or mRNA corresponding to intercalated cells in the kidney organoid is higher than that in a kidney organoid differentiated from a metanephric mesenchyme cell aggregate formed under a normoxic condition, the hypoxic condition is a condition with an oxygen concentration of more than 1% to less than 10%, and the normoxic condition is a condition with an oxygen concentration of 10% or more.

According to a further aspect of the present disclosure, there may be provided a kidney organoid differentiated from a metanephric mesenchyme cell aggregate in a permeable microwell, wherein the expression level of at least one of mRNA corresponding to podocytes, mRNA corresponding to proximal tubules, or mRNA corresponding to distal tubules in the kidney organoid is higher than that in a kidney organoid differentiated from a metanephric mesenchyme cell aggregate formed in an impermeable microwell.

According to a further aspect of the present disclosure, there may be provided a medium composition for differentiating metanephric mesenchyme cell aggregates, differentiated from stem cells, into kidney organoids, the medium composition containing FBS. Here, the FBS may be contained in an amount of 0.5 vol % to 5 vol % based on the total weight of the medium composition. In addition, the medium composition may further contain 25 ng/ml to 50 ng/ml of FGF9.

According to the present disclosure, the success rate of differentiation may be increased by the application of a new protocol, and it is possible to form a clearer tubular structure, and furthermore, it is possible to generate kidney organoids, which express improved nephron function, by utilizing permeable wells. Therefore, when the kidney organoids obtained according to the present disclosure are used, they may mimic, in vitro, phenomena such as actual kidney diseases and drug uptake in fields such as studies on kidney-related diseases and evaluation of nephrotoxic drugs, in which in vitro kidney models are used. Thus, the kidney organoids may be widely used in the pharmaceutical field and the tissue engineering field.

DETAILED DESCRIPTION

Figure 1:
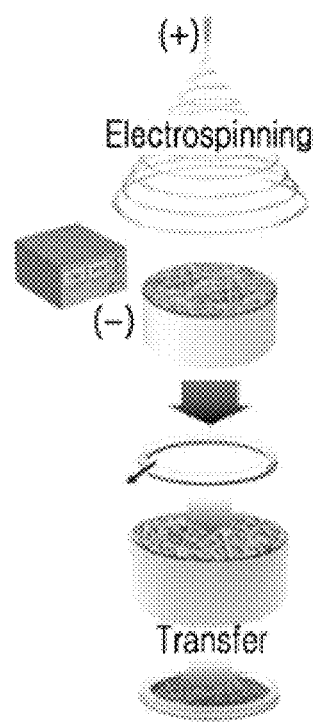
FIGS. 1(a) to 1(c) show exemplary processes of fabricating permeable microwells, which may be applied to the present disclosure, and fabricated wells.

Hereinafter, preferred embodiments of the present disclosure will be described with reference to the accompanying drawings. However, the embodiments of the present disclosure may be modified in various other forms, and the scope of the present disclosure is not limited to the embodiments described below.

A method for producing kidney organoids according to the present disclosure includes steps of: (1) differentiating stem cells into metanephric mesenchyme cells; (2) forming metanephric mesenchyme cell aggregates by culturing the metanephric mesenchyme cells; and (3) differentiating the metanephric mesenchyme cell aggregates into kidney organoids.

The stem cells that may be used in the present disclosure may be at least one cell type selected from among induced pluripotent stem cells (iPSCs) and embryonic stem cells (ESCs). For example, the stem cells may be induced pluripotent stem cells (iPSCs).

A basal medium that may be used in the present disclosure may use a basal medium that is used for culturing animal cells, and examples thereof include IMDM, Medium 199, Eagle's Minimum Essential Medium (EMEM), αMEM, Dulbecco's Modified medium Eagle's Medium (DMEM), Ham'sF12 (F12) medium, RPMI 1640 medium, advanced RPMI 1640 medium, Fischer's medium, McCoy's 5A medium, basal medium Eagle's (BME), MCDB media, and mixed media thereof. For example, advanced RPMI 1640 is preferable because it contains less FBS than RPMI 1640 and enables a more reproducible experiment without changing the cell growth rate or the morphology and function of cells.

If necessary, the medium may contain, for example, at least one serum replacement selected from among albumin, transferrin, knockout serum replacement (KSR) (serum replacement in ES cell culture; Invitrogen), N2 supplement (Invitrogen), B-27™ supplement (Invitrogen), fatty acids, insulin, a collagen precursor, trace elements, 2-mercaptoethanol, 3'-thiol glycerol, and the like, and may also contain at least one selected from lipids, amino acids, L-glutamine, GLUTAMAX™ (L-glutamine) (Invitrogen), non-essential amino acids (NEAA), vitamins, growth factors, antibiotics, antioxidants, pyruvic acid, buffers, inorganic salts, and equivalents thereto. A pre-optimized medium for stem cell culture, such as ReproFF2 (reproCELL), STEMFIT® stem cell culture basic medium (Ajinomoto), or the like, may be used.

Meanwhile, step (1) of stem cells into metanephric mesenchyme cells is preferably performed in a hypoxic atmosphere with an oxygen concentration of more than 1% to less than 10%, for example, an oxygen concentration of more than 1% to less than 5%. If the oxygen concentration in step (1) is 10% or higher, a problem arises in terms of the stable induction of a dome-like morphology, which should appear preferably on about day 4 in step (1), which is the initial stage of differentiation. In addition, as a result of performing differentiation until day 9 under a condition with an oxygen concentration of 1% in step (1), it was confirmed that the formed kidney organoids were relatively small in size, and the number of the formed organoids was significantly smaller than the number of organoids formed by differentiation under a condition with an oxygen concentration of 5%, indicating that, under a condition with an oxygen concentration of 1% or less, a problem arises in that differentiation is unstable.

In the early stage of the development of actual human embryos, the development of human embryos proceeds in a hypoxic environment due to the absence of vascularization, and kidney development under such hypoxic conditions enhances tubule formation through activation of the hypoxia inducer HIF. Based on this fact, in the present disclosure, the atmosphere in step (1), which is the initial stage in differentiation into kidney organoids, set to a hypoxic condition, which is an embryonic development environment. Meanwhile, in step (2) and step (3), differentiation was performed under a normoxic condition. As such, kidney organoids differentiated in step (1) under a hypoxic condition according to the new protocol may show a clear tubular structure with higher reproducibility than kidney organoids differentiated under non-hypoxic conditions, after completion of step (3), for example, on day 21.

On the other hand, step (1) of differentiating stem cells into metanephric mesenchyme cells may include a step of culturing stem cells in at least one medium selected from among i) a medium containing a GSK-3β inhibitor and a BMP4 inhibitor, ii) a medium containing Activin A, iii) a medium containing FGF9, and a medium obtained by mixing two or more of these media, and may be performed for 8 to 10 days.

For example, step (1) of differentiating stem cells into metanephric mesenchyme cells preferably include a step of culturing stem cells sequentially in i) a medium containing a GSK-3β inhibitor and a BMP4 inhibitor, ii) a medium containing Activin A, and iii) a medium containing FGF9, for 1 to 4 days in each medium. For example, the stem cells may be cultured for about 4 days in i) a medium containing a GSK-3β inhibitor and a BMP4 inhibitor, about 3 days ii) a medium containing Activin A, and about 3 days iii) a medium containing FGF9.

Examples of the BMP4 inhibitor include proteinaceous inhibitors such as chordin, NOGGIN, and follistatin, Dorsomorphin (6-[4-(2-piperidin-1-yl-ethoxy)phenyl]-3-pyridin-4-yl-pyrazolo[1,5-a]pyrimidine), LDN193189 (4-(6-(4-(piperazin-1-yl)phenyl)pyrazolo[1,5-a]pyrimidin-3-yl) quinoline), Gremlin (Grem1), Sclerostin, twisted gastrulation (Tsg) protein, and the like. The BMP4 inhibitor is more preferably NOGGIN and may be used at a concentration of, for example, 1 to 100 ng/ml, preferably 5 to 20 ng/ml.

Examples of the GSK-3β inhibitor include CHIR, CHIR99021, and the like. The concentration of the GSK-3β inhibitor may be appropriately selected by those skilled in the art depending on the kind of GSK-3β inhibitor used, but is, for example, 0.01 μM to 100 μM, preferably, 0.1 μM to 10 μM.

Step (2) of forming metanephric mesenchyme cell aggregates is preferably performed for 2 days to 3 days in a medium containing a GSK-3β inhibitor and FGF9.

Meanwhile, the concentration of FGF9 in the medium used in step (1) and step (2) is 5 ng/ml to less than 25 ng/ml. If the FGF9 concentration is less than 5 ng/ml, a problem arises in terms of the development and maintenance of nephron stem cells, and if the FGF9 concentration is 25 ng/ml or more, a problem arises in that the efficiency of differentiation into kidney organoids is unstable.

Step (3) of differentiating the metanephric mesenchyme cell aggregates into kidney organoids may be performed in a medium containing FBS for 7 days to 100 days, for example, 10 days to 50 days, or 15 days to 30 days, for example, 16 days to 21 days. For example, step (3) is performed for 7 days to 100 days in a medium containing FBS in an amount of 0.5 to 5 vol % based on the total volume of the medium composition. If the FBS concentration is less than 0.5 vol %, a problem arises in that the nephron structures of formed kidney organoids are hardly observed, and if the FBS concentration is more than 5 vol %, a problem arises in terms of differentiation into kidney organoids, because FBS may affect the growth rate of cells or the expression of genes and proteins and change the phenotype of the cells.

When the medium contains FBS as described above, differentiation may be successfully performed while maintaining the cell viability until the completion of differentiation by supplying growth factors, ECM molecules, hormones, etc., contained in FBS, to three-dimensional kidney organoids.

Meanwhile, step (3) of differentiating the metanephric mesenchyme cell aggregates into kidney organoids includes a step of culturing the cell aggregates for 2 to 5 days in a medium containing FGF9 at a concentration of 25 ng/ml to 50 ng/ml, for example, 25 ng/ml to 40 ng/ml. Step (3) is preferably performed in a medium containing a high concentration of FGF9, unlike steps (1) and (2) which are performed in media containing a low concentration of FGF9. If the FGF9 concentration in step (3) is less than 25 ng/ml, a problem arises in that kidney organoids may not have a developed tubular structure, and if the FGF9 concentration is more than 50 ng/ml, a problem arises in terms of stable differentiation into kidney organoids, because FGF9 affects the cell proliferation rate.

Meanwhile, the step of culturing the cell aggregates for 2 days to 5 days in a medium further containing 25 ng/ml to 50 ng/ml of FGF9 may be included at the beginning or initial stage of step (3). Preferably, the step of culturing the cell aggregates is performed using a medium further containing 25 ng/ml to 50 ng/ml of FGF9 for 2 to 5 days from the start of step (3).

When differentiation into cell aggregates in step (2) occurs, growth factors are not sufficiently delivered to the cell aggregates. For this reason, the concentration of FGF9 required for growth and maintenance of nephron stem cells in step (3) is increased to 25 ng/ml to 50 ng/ml, whereby differentiation into tubular structures may be more successfully enhanced.

Meanwhile, in the present disclosure, step (2) and step (3) are preferably performed in microwells. In this case, the microwell may include at least one concave portion. Preferably, the at least one concave portion is formed at the bottom of the microwell. Meanwhile, the microwell is preferably a porous microwell, and the porous microwell may be formed of a porous membrane. For example, technology related to a porous microwell described in Korean Patent No. 10-2224065 B1 may be employed.

When differentiation into kidney organoids is performed the protocol of the present disclosure as described above, the success rate of differentiation is uniform, and thus the stable and reproducible formation of kidney organoid is possible.

According to the protocol provided by the method for producing kidney organoids according to the present disclosure, the success rate of differentiation may be increased, and furthermore, the smooth formation of tubular structures is possible.

Hereinafter, the present disclosure will be described in more detail with reference to specific examples. The following examples are merely to aid in the understanding of the present disclosure, and the scope of the present disclosure is not limited thereto.

EXAMPLES

1. Production of Kidney Organoids

Example 1

Inducible pluripotent stem cells (iPSCs) (IMR90-4, WiCell or WTC-11, CORIELL INSTITUTE) at a density of 25,000 to 30,000 cells/well were seeded in a 24-well plate coated with 1% Geltrex. In this case, mTeSR™1 containing 10 μM of Y-27632 was used as a medium. One day later, the medium was replaced with fresh mTeSR™1 medium, and it was confirmed that the stem cells (iPSCs) started to form colonies.

From the time when the stem cell (iPSC) colonies filled about 35% to 40% of the wells, a step of differentiating the cells in a differentiation medium in a hypoxic condition with an oxygen concentration of 5% was started (day 0). As the differentiation medium, an advanced RPMI 1640 medium (a medium having a lower FBS content than RPMI 1640) containing 10 μM of CHIR, GLUTAMAX™ 100X (i.e., 1 vol % based on the total volume of the medium composition) (L-glutamine) and 10 ng/ml of Noggin was used, and the step was performed in a hypoxic environment (5% $O_2$). On day 2, the medium was replaced with a fresh differentiation medium, and on day 4, when the cell morphology became a dome-like morphology, the cells were treated with Activin A medium. Here, as the Activin A medium, an advanced RPMI 1640 medium containing 10 ng/ml of Activin A and GLUTAMAX™ 100X (1 vol % based on the total volume of the medium composition) (L-glutamine) was used. On day 7, the cells were treated with a medium containing a low concentration of FGF9. Here, as the medium containing a low concentration of FGF9, an advanced RPMI medium containing 10 ng/ml of FGF9 and GLUTAMAX™ 100X (1 vol % based on the total volume of the medium composition) (L-glutamine) was used.

Figure 1B:
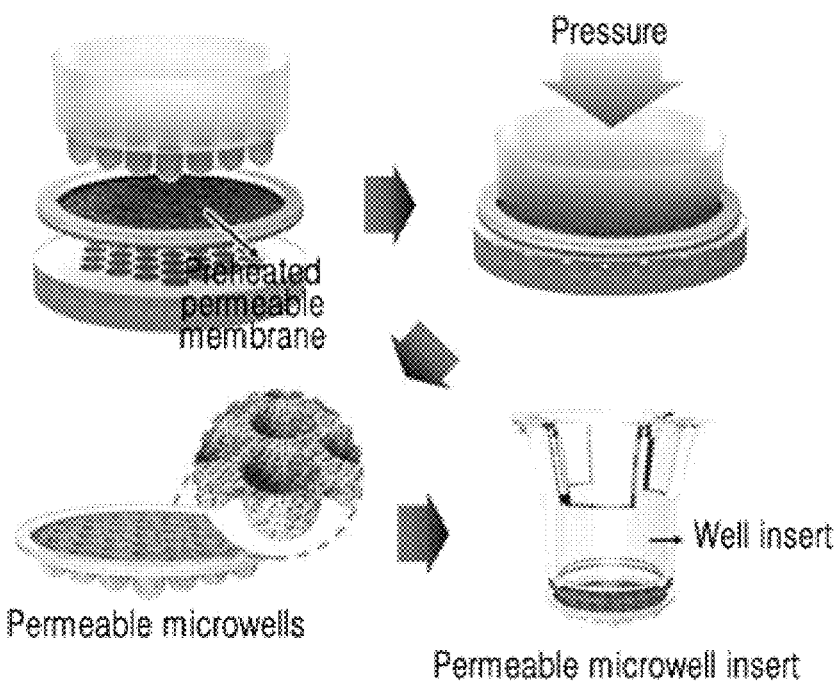
Figure 1C:
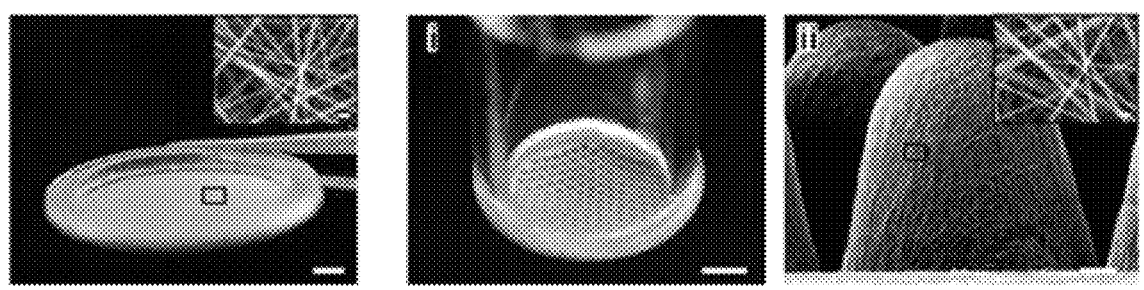
Figure 2A:
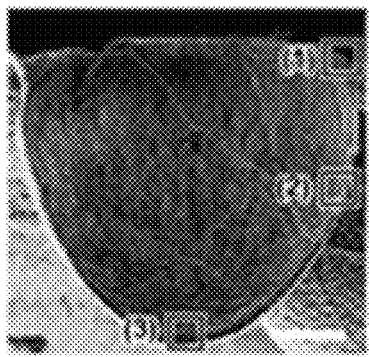
FIGS. 2(a) and 2(b) show cross-sections of a permeable well that may be applied to the present disclosure.
Figure 2B:
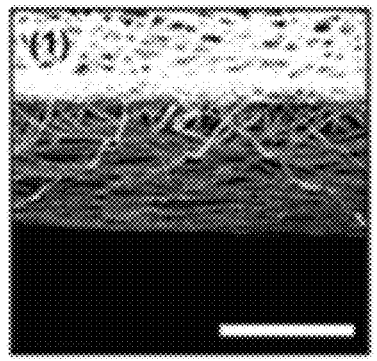
Figure 2B:
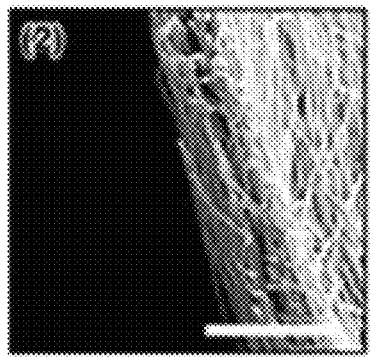
Figure 2B:
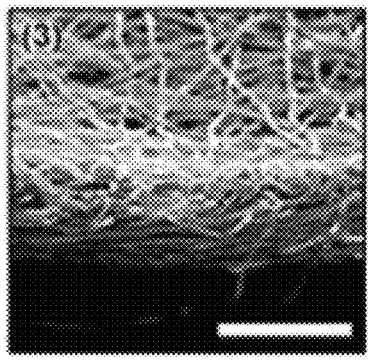

Permeable wells used in this Example may be fabricated as shown in FIG. 1(a). Specifically, a permeable membrane is fabricated by an electrospinning process using a 5% to 25% solution obtained by mixing polycaprolactone and Pluronic 108 at a ratio of 5:5 in a hexafluoro-2-propanol solution. Then, as shown in FIG. 1(b), permeable wells may be fabricated by subjecting the permeable membrane to a thermoforming process using a negative mold and a positive mold. It can be seen that the permeable wells fabricated in this way have a porous structure (FIG. 1(c)). A cross-section of the permeable well used in the present disclosure is shown in FIG. 2.

On day 9, the metanephric mesenchyme cells differentiated from the stem cells were detached from the well plate by Accutase treatment, and then seeded in permeable wells at a density of 20,000 cells/well based on 800 μM. In this case, an advanced RPMI 1640 medium containing 3 μM of CHIR, 10 ng/ml of FGF9 and GLUTAMAX™ 100X (1 vol % based on the total volume of the medium composition) (L-glutamine) was used as a medium. From day 9, the cells were cultured in an environment with an oxygen concentration of 21% to form cell aggregates.

On day 11, the medium was replaced with a medium containing a high concentration of FGF9. Here, as the high-concentration FGF9 medium, an advanced RPMI 1640 medium containing 30 ng/ml of FGF9 and GLUTAMAX™ 100X (1 vol % based on the total volume of the medium composition) (L-glutamine) was used, and the cells were differentiated into kidney vesicles by culturing in an environment with an oxygen concentration of 21%.

On day 14, the cells were cultured up to day 21 using, as a basal differentiation medium, an advanced RPMI 1640 medium containing FBS in an amount of 1.5 vol % based on the total volume of the medium and GLUTAMAX™ 100X (1 vol % based on the total volume of the medium composition) (L-glutamine).

Figure 3:
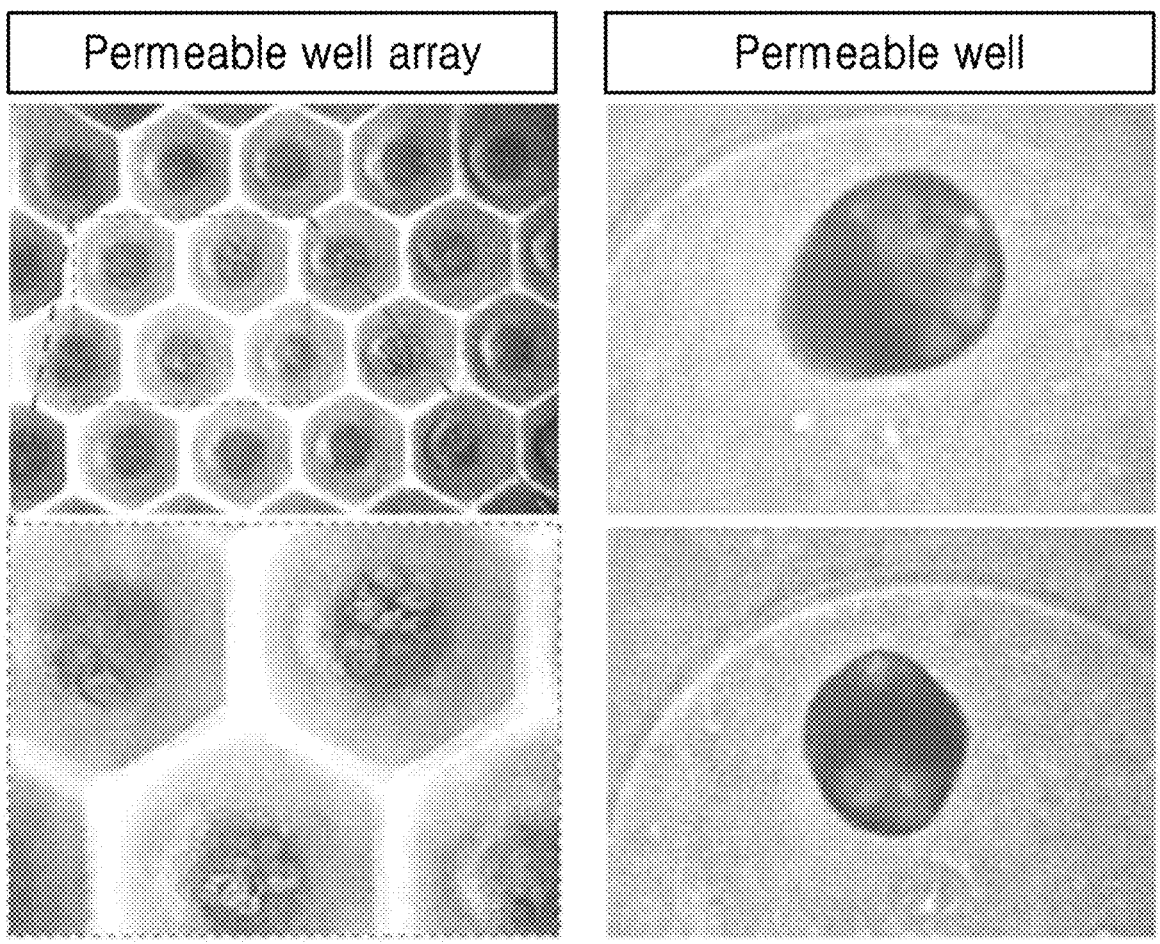
FIG. 3 shows kidney organoids formed on permeable wells in an example of the present disclosure.

As a result, as shown in FIG. 3, it could be confirmed that kidney organoids were formed on the permeable wells.

Comparative Example 1

Kidney organoids were produced in the same manner as in Example 1, except that impermeable wells (Aggrewell™) were used instead of the permeable wells.

2. Examination of Difference in Kidney Organoids Depending on Well Types (1) Analysis of Uniformity of Differentiation On day 21 of differentiation, the differentiated kidney organoids were washed with DPBS for 5 minutes and then fixed by 2 hours of treatment with PFA in an amount of 4 vol % based on the total solution volume. After 2 hours, the kidney organoids were washed three times with DPBS for 10 minutes per wash and blocked at room temperature by treatment with TRITON® X-100 (octylphenol ethoxylate) in an amount of 0.3 vol % and donkey serum in an amount of 5 vol % based on the total buffer volume. After treatment for 2 hours, primary antibody was diluted in a buffer containing TRITON® X-100 (octylphenol ethoxylate) in an amount of 0.3 vol % and bovine serum albumin (BSA) in an amount of 0.5 vol % based on the total buffer volume, and the kidney organoids were treated with the dilution at 4° C. for 5 days. The kidney organoids were washed three times with PBST containing TRITON® X-100 (octylphenol ethoxylate) in an amount of 0.3 vol % based on the total buffer volume at room temperature for 10 minutes per wash. Secondary antibody was diluted in a buffer containing TRITON® X-100 (octylphenol ethoxylate) in an amount of 0.3 vol % and bovine serum albumin (BSA) in an amount of 0.5 vol % based on the total buffer volume, and the kidney organoids were treated with the dilution overnight at 4° C. The next day, the kidney organoids were washed three times with PBST containing TRITON® X-100 (octylphenol ethoxylate) in an amount of 0.3 vol % based on the total buffer solution at room temperature for 20 minutes per wash. DAPI was diluted in DPBS at a concentration of 1 μg/ml, and the kidney organoids were treated with the dilution overnight at 4° C. and then washed three times with DPBS for 10 minutes. According to this process, immunofluorescence staining experiments were performed on the kidney organoids produced in Example 1 and Comparative Example 1.

Figure 4A:
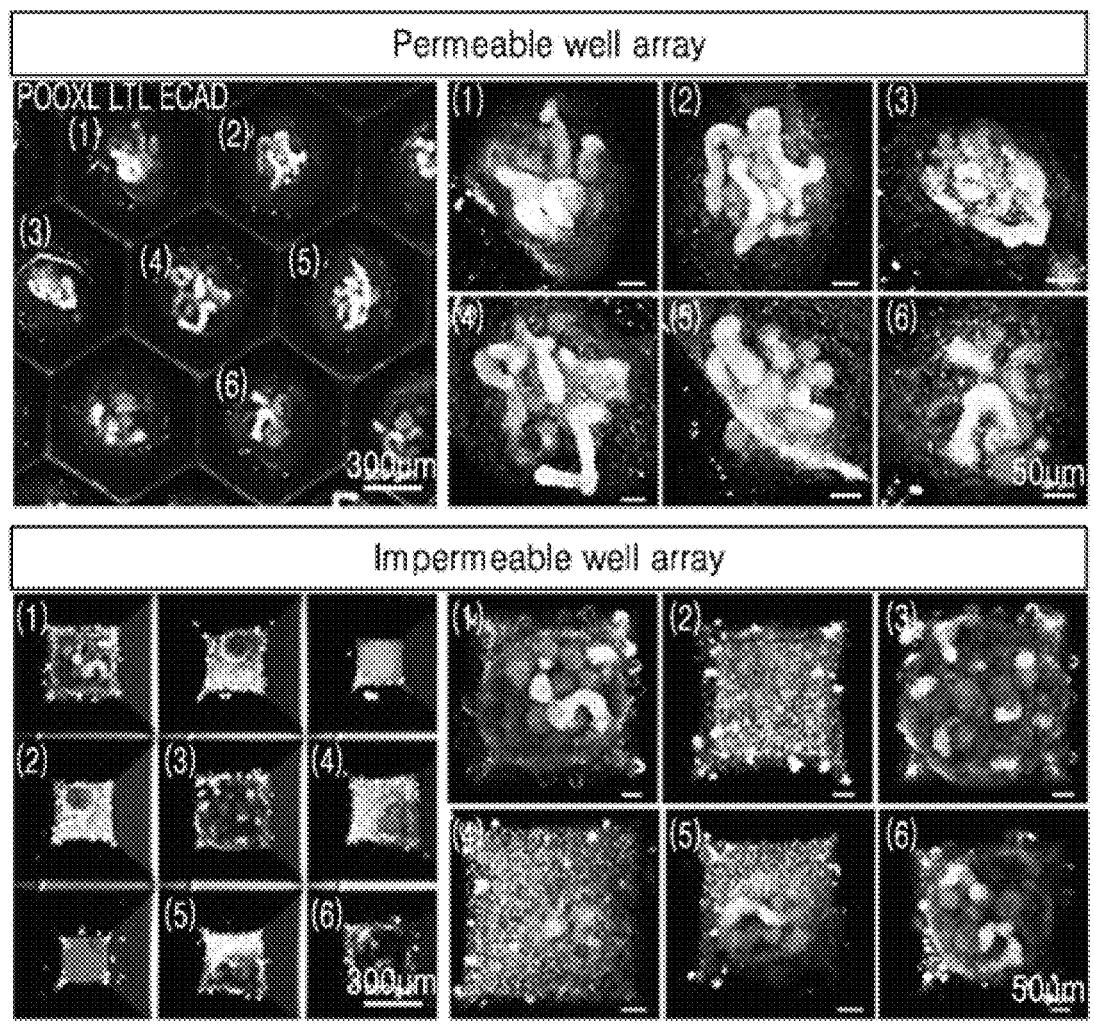
FIGS. 4(a) and 4(b) show the results of immunofluorescence staining of kidney organoids formed in an impermeable well array and kidney organoids formed in a permeable well array.
Figure 4B:
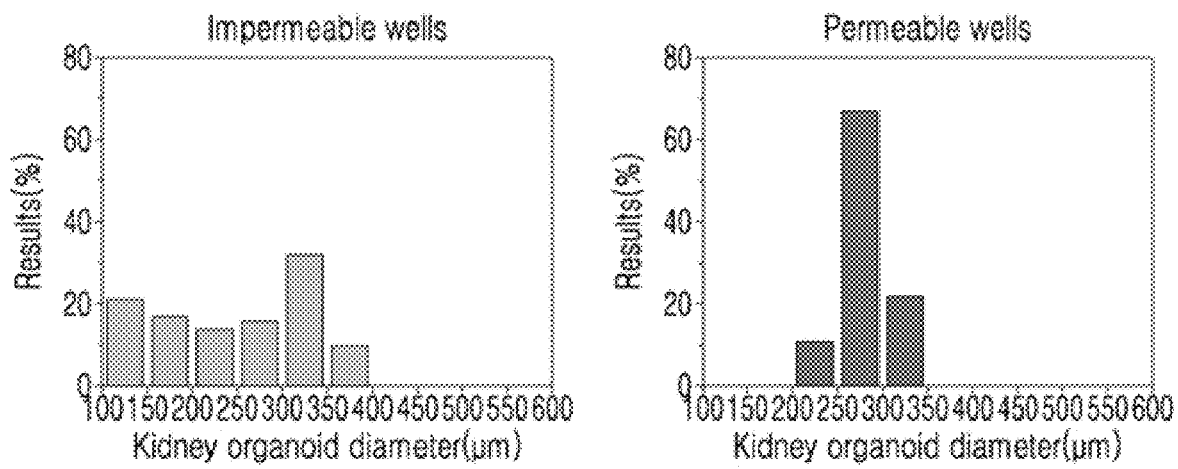

As a result of immunofluorescence staining of the kidney organoids formed in the impermeable well array and the kidney organoids formed in the permeable well array, as shown in FIG. 4(a) showing a comparison of PODXL (podocyte), LTL (proximal tubule epithelial cell) and ECAD (distal tubule epithelial cell) markers present in the kidney nephron, it could be confirmed that the kidney organoids formed in the permeable well array in Example 1 according to the present disclosure were uniformly well differentiated, whereas the kidney organoids formed in the impermeable well array in Comparative Example 1 had poor uniformity. In addition, as a result of quantitatively examining the uniformity, as shown in FIG. 4(b), it could be confirmed that the diameter of the kidney organoids formed in the impermeable well array ranged from 100 μm to 400 μm, and the diameter of the kidney organoids formed in the permeable well array was distributed within the range of 200 μm to 350 μm. That is, it can be seen that the kidney organoids formed in an impermeable well array were non-uniformly differentiated kidney organoids having different diameter values, whereas the kidney organoids formed in the permeable well array were uniformly differentiated kidney organoids having relatively similar diameter values.

(2) Analysis of Kidney Organoid Maturity

Using induced pluripotent stem cells (iPSCs) as a control, maturity of the differentiated renal organoids was analyzed by quantifying markers expressed in the kidney organoids according to the reverse transcription polymerase chain reaction (RT-qPCR) method. The experiment was conducted under the following conditions: treatment at 95° C. for 1 min, and then 40 cycles, each consisting of 95° C. for 15 sec, 56° C. or 62.7° C. for 15 sec, and 72° C. for 45 sec. According to this process, an experiment was performed to analyze the maturity of the kidney organoids produced in each of Example 1 and Comparative Example 1.

Figure 5:
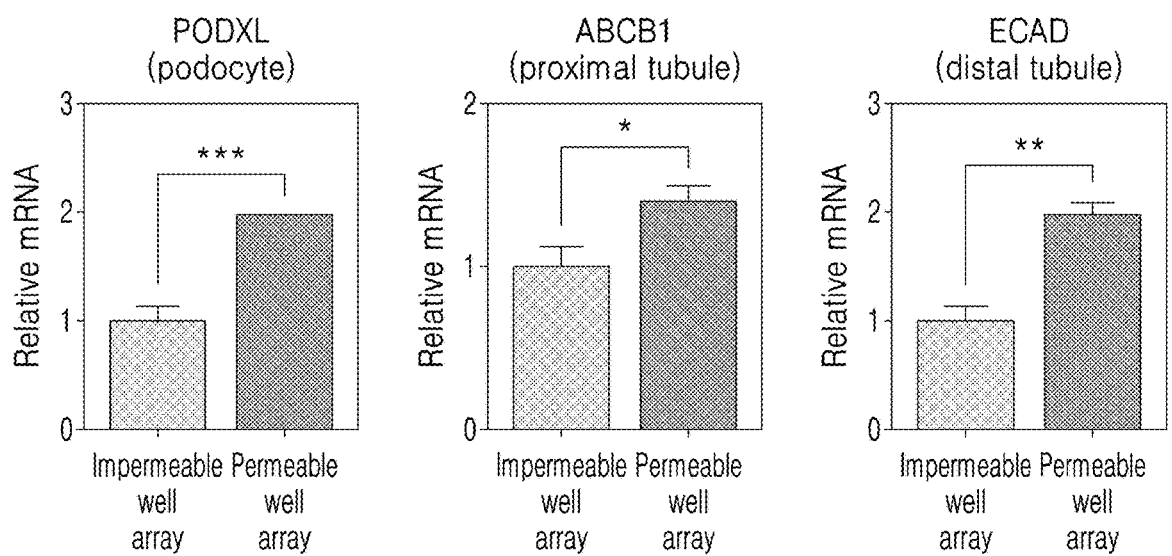
FIG. 5 shows the results of comparing maturity between kidney organoids formed in an impermeable well array and kidney organoids formed in a permeable well array.

As a result, as shown in FIG. 5 showing a comparison of PODXL (podocyte), LTL (proximal tubule epithelial cell), and ECAD (distal tubule epithelial cell) markers present in the nephron of the kidney, it could be confirmed that the expression levels of the markers in the kidney organoids formed in the permeable well array in Example 1 were higher than those in the kidney markers formed in the impermeable well array in Comparative Example 1. Specifically, the expression levels of mRNA corresponding to podocytes (PODXL), mRNA corresponding to LTL (proximal tubule epithelial cells), and mRNA corresponding to ECAD (distal tubule epithelial cells) in the kidney organoids formed in the permeable well array were more than 1-fold to no more than 2-fold higher than those in the kidney organoids formed in the impermeable well array.

Figure 6:
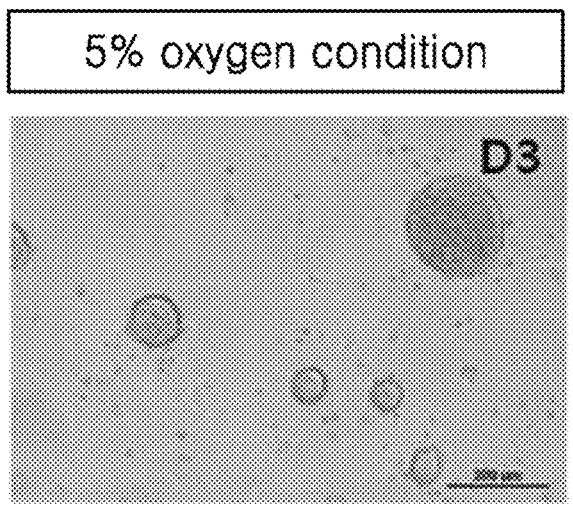
FIG. 6 shows the difference depending on oxygen concentration conditions in step (1).
Figure 6:
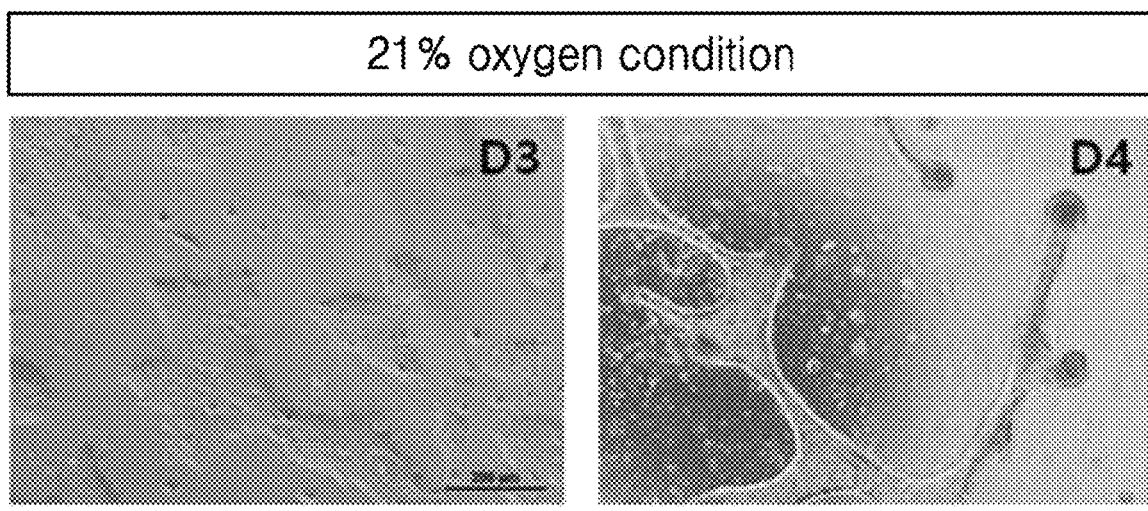

3. Examination of Difference in Kidney Organoids Depending on Protocols (1) Difference Depending on Oxygen Concentration in Step (1) of Differentiating Cells Kidney organoids were produced in the same manner as in Example 1, except that differentiation in step (1) was performed at an oxygen concentration of 21%, not under hypoxic conditions. In this case, as shown in FIG. 6, it was confirmed that the cell morphology was not a dome-like morphology even on day 4 of differentiation (right photograph). However, it was confirmed that, when differentiation was performed under a hypoxic condition with an oxygen concentration of 5%, the dome-like morphology appeared on day 3, was maintained up to day 4, and appeared stably in each batch on day 4 of differentiation (left photograph).

Figure 7A:
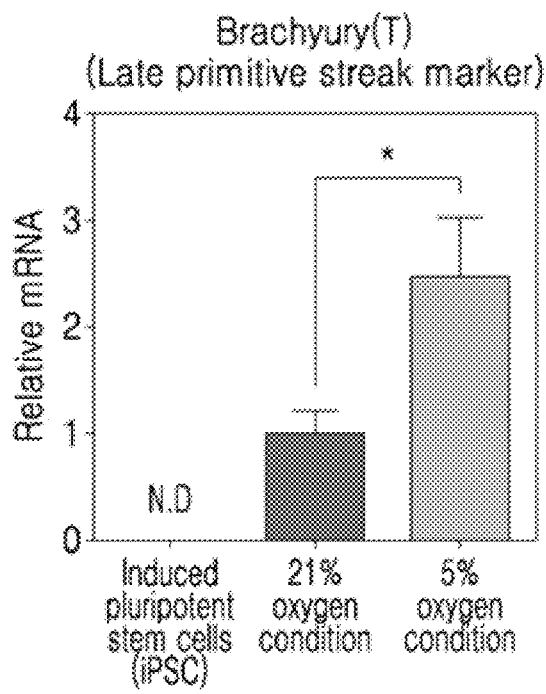
FIG. 7(a) is a graph showing the results of analyzing the expression level of the late primitive streak marker Brachyury (T) by reverse transcription-polymerase chain reaction in order to confirm the difference depending on oxygen concentration conditions in step (1), and 7(b) shows the results of immunofluorescence staining analysis of kidney organoids formed on day 21 of differentiation, and indicates that the nephron structure is clearer under a hypoxic condition (5% oxygen concentration).
Figure 7B:
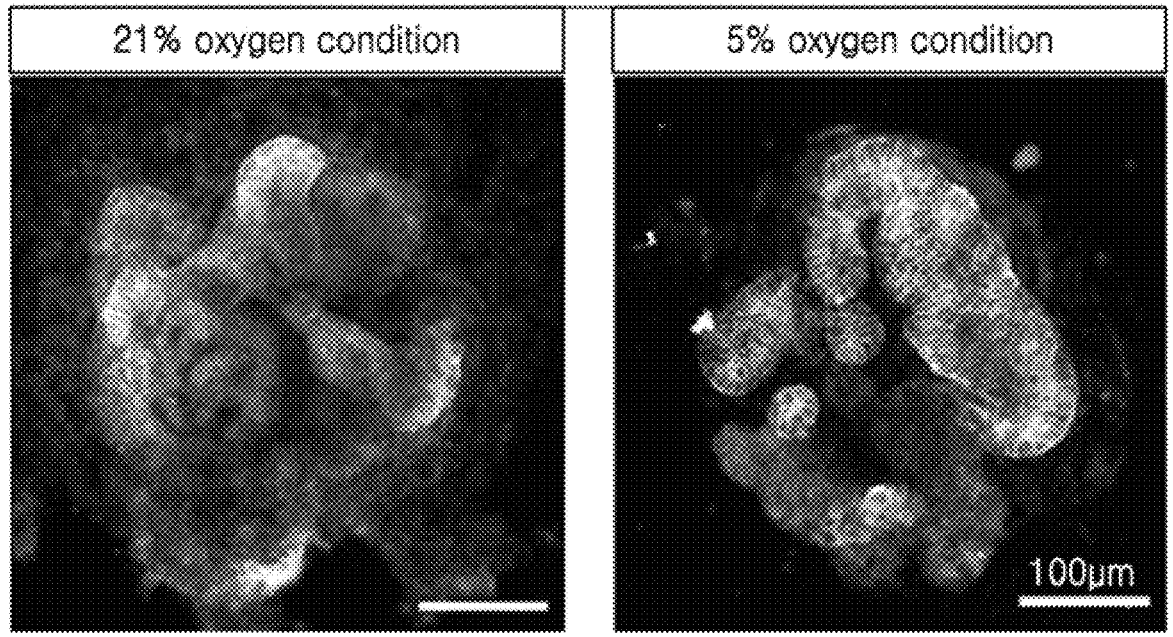

As a result of analyzing the expression level of the late primitive streak marker Brachyury (T) by reverse transcription polymerase chain reaction for clearer confirmation, as shown in FIG. 7(a), was confirmed that the expression level of the late primitive streak marker Brachyury (T) in the kidney organoids differentiated in a hypoxic environment (5%) was higher than that in the kidney organoids differentiated in an environment with an oxygen concentration of 21%. Furthermore, as a result of immunofluorescence staining analysis on day 21 of differentiation, it was observed that the nephron structure more clearly appeared under the hypoxic condition (5% oxygen concentration) (FIG. 7(b)).

Figure 8A:
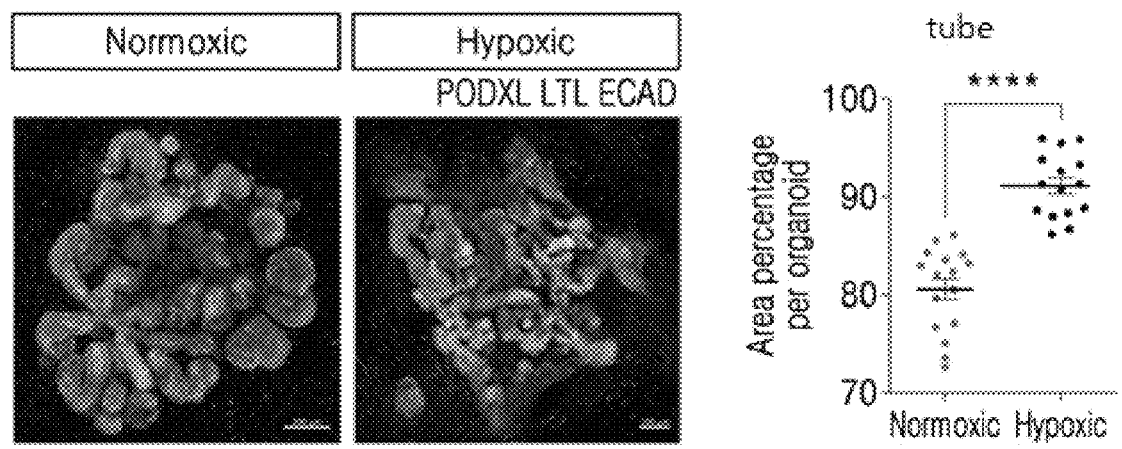
FIGS. 8(a) to 8(c) and 9(a) to 9(d) show the results of observing the tubular structure or connection structure in differentiated kidney organoids depending on oxygen concentration conditions.
Figure 8B:
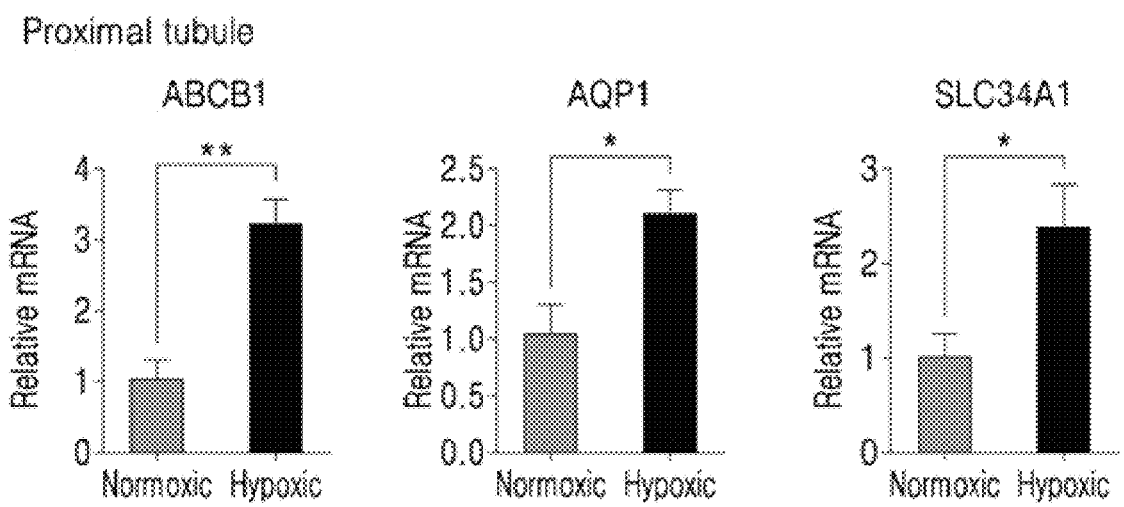
Figure 8C:
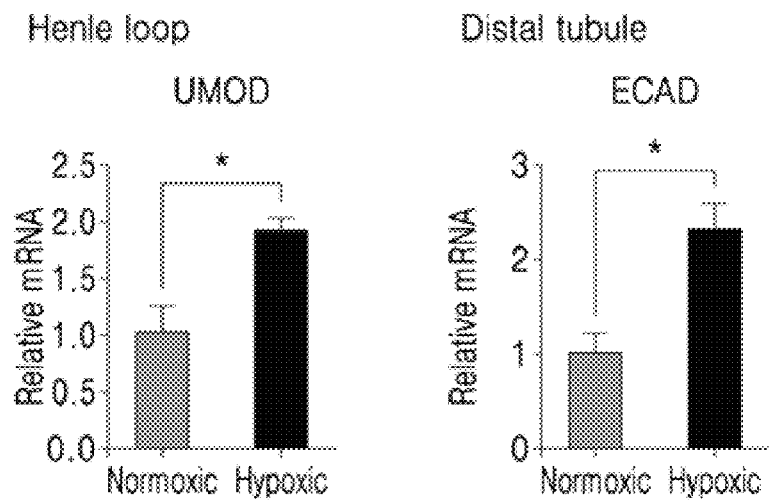

In addition, immunofluorescence staining experiments were performed to compare between the kidney organoids differentiated up to day 9 under a hypoxic condition (oxygen concentration of 5%) and the kidney organoids differentiated up to day 9 under a normoxic condition (for example, an environment with an oxygen concentration of 21%) according to a conventional existing protocol. In this case, it could be confirmed that there was a significant difference between the two types of kidney organoids. Specifically, as shown in FIG. 8(a), it could be confirmed that the tubular structure stained by the proximal tubule (LTL) marker and the distal tubule (ECAD) marker was longer in the kidney organoids differentiated under the hypoxic condition than that observed in the kidney organoids differentiated under the normoxic condition. In addition, as a result of quantitatively analyzing the tubules, it could be confirmed that the percentage of stained tubule markers per organoid was higher in the kidney organoids differentiated under the hypoxic condition than in the kidney organoids differentiated under the normoxic condition. FIG. 8(b) depicts graphs comparing the mRNA expression levels of each tubule marker between a normoxic condition and a hypoxic condition. As shown therein, it could be confirmed that the expression levels of mRNAs (ABCB1, AQP1, and SLC34A1) corresponding to proximal tubules, mRNA (UMOD) corresponding to Henle loops, and mRNA (ECAD) corresponding to distal tubules were higher in the organoid differentiated under the hypoxic condition than in the organoids differentiated under the normoxic condition. More specifically, the organoids differentiated under the hypoxic condition were 3-fold or higher in ABCB1 mRNA expression level, 2-fold or higher in AQP1 mRNA expression level, 2-fold or higher in SLC34A1 mRNA expression level, 1.5-fold or higher in UMOD mRNA expression level, and 2-fold or higher in ECAD mRNA expression level than those differentiated under the normoxic condition.

On the other hand, the kidney organoids formed under a hypoxic condition (5% oxygen concentration) had a longer tubular structure than the kidney organoids formed under a normoxic condition as described above, and also showed a pattern in which adjacent organoids were connected to each another as the tube structure became longer. It is known that the human nephron structure has a structure in which nephrons are connected to each other by connecting tubules deep in the cortex. The observation that adjacent organoids are connected by a long tubular structure under the hypoxic condition suggests that the kidney organoids formed under the hypoxic condition are similar in structure to actual human nephrons.

Figure 9A:
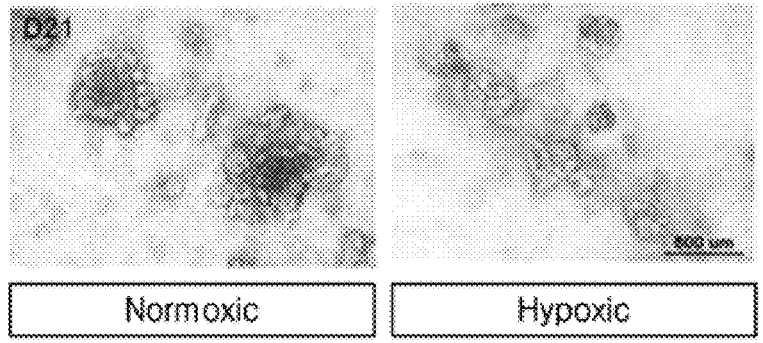
Figure 9B:
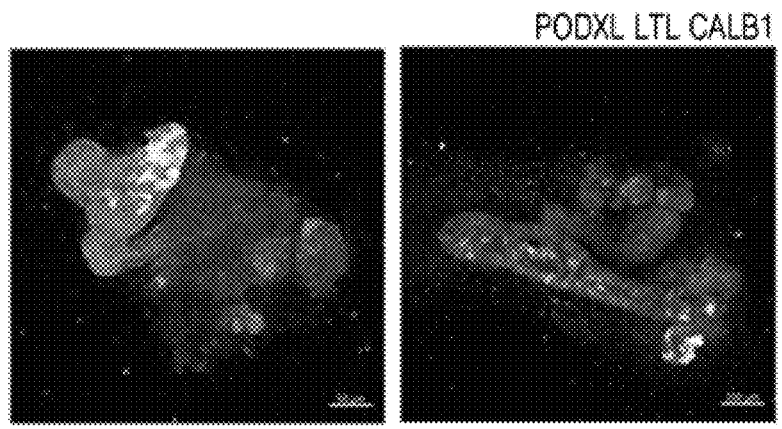
Figure 9C:
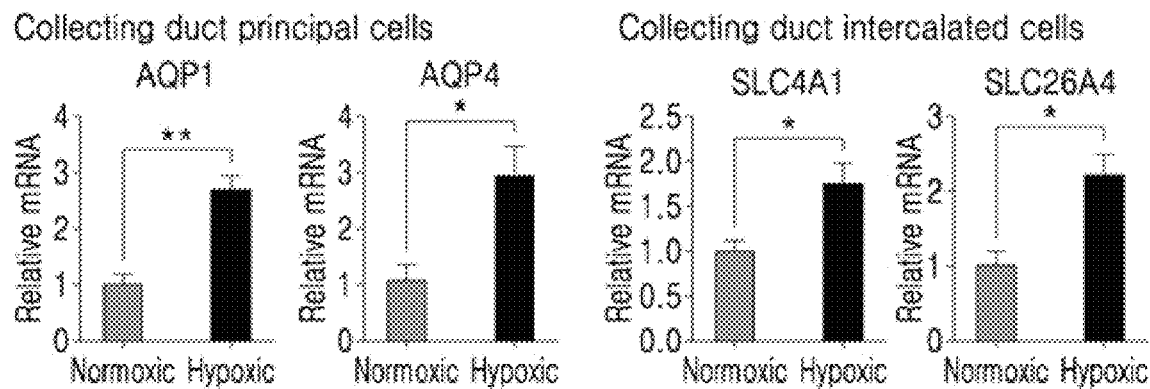
Figure 9D:
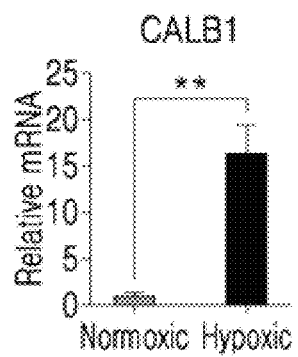

FIGS. 9(a) to 9(d) show the results of observing and comparing and observing the connection structure in the kidney organoids formed under a normoxic condition (21% oxygen environment) and the connection structure in the kidney organoids formed under a hypoxic condition (5% oxygen environment). Referring to FIG. 9(a), it can be confirmed that a special connection structure is not seen between adjacent organoids in the photograph under the normoxic condition, whereas a tubular structure is formed between adjacent organoids under the hypoxic condition. In addition, FIG. 9(b) shows the results of staining the ECAD marker in both the distal tubules and the collecting ducts and the CALB1 marker in the collecting ducts. As shown therein, it can be confirmed that, unlike the normoxic condition on the left side, the CALB1 marker is clearly visible in the elongated tubular structure connecting between adjacent organoids under the hypoxic environment on the right side, indicating that the collecting duct is structurally formed in adjacent organoids among the organoids differentiated under a hypoxic condition. For reference, the left photograph of FIG. 9(b) is shown on a scale of 1:50 μm, and the right photograph is shown on a scale of 1:100 μm. In addition, FIG. 9(c) depicts graphs comparing three types of cells constituting the collecting ducts and the expression levels of a total of four gene markers, including AQP2 and AQP4 (principal cells), SLC4A1 (type alpha intercalated cells), and SLC26A4 (type beta intercalated cells). As shown therein, the organoids differentiated under the hypoxic condition were 2-fold or higher in AQP2 mRNA expression level, 2-fold or higher in AQP4 mRNA expression level, 1.5-fold or higher in SLC4A1 mRNA expression level, and 2-fold or higher in SLC26A4 mRNA expression level than those differentiated under the normoxic condition. On the other hand, as a result of observing the kidney organoids differentiated under the hypoxic condition on day 21, as shown in FIG. 9(d), it was confirmed that the expression level of CALB1 gene, which is the principal cell marker of the collecting duct, in the kidney organoids differentiated under the normoxic condition, was 15-fold higher than that in the kidney organoids differentiated under the hypoxic condition.

Figure 10A:
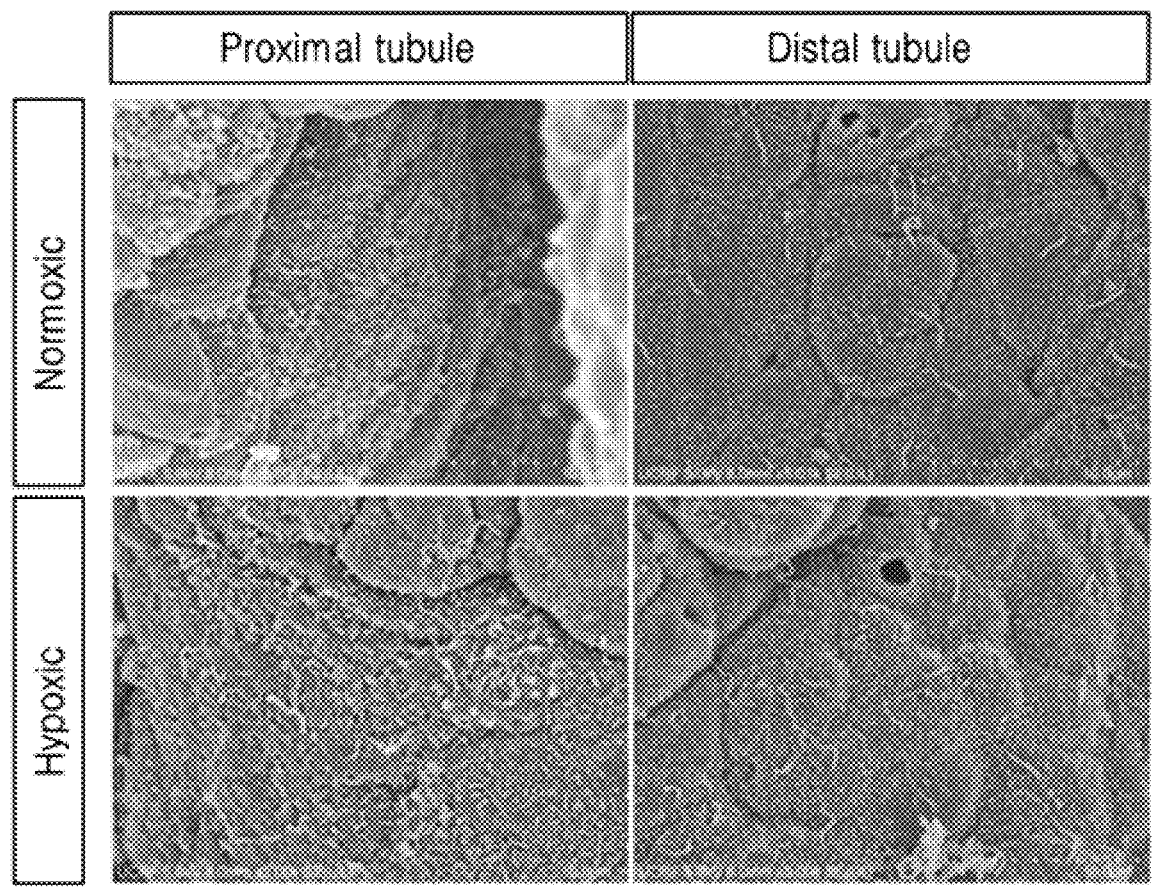
FIGS. 10(a) and 10(b) show the results of observing and comparing the surfaces of cells in kidney organoids depending on oxygen concentration conditions.
Figure 10B:
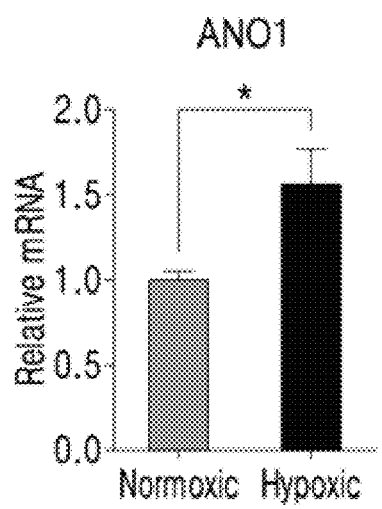

FIG. 10(a) depicts SEM images showing a comparison of the cell surface between the kidney organoids differentiated under a normoxic condition (21% oxygen concentration) and the kidney organoids differentiated under a hypoxic condition (5% oxygen concentration). It is known that the proximal tubule epithelial cells in the human kidney have one long primary cilium and microvilli present around the same, and the distal tubule epithelial cells have only one long primary cilium without microvilli. Here, it is also known that the primary cilia play a role in maintaining the structure and function of the nephron in the kidney. Referring to the images in FIG. 10 (a), it could be confirmed that the organoids differentiated under the hypoxic condition had proximal tubule microvilli formed at a higher density, and the length of proximal tubule and distal tubule primary cilia therein were also longer than that in the organoids differentiated under the normoxic condition and was similar to the length of human cilia. FIG. 10(b) compares the gene expression level of ANO1, a protein that is expressed in primary cilia and affects cilia development, and as shown therein, it was observed that the expression level of ANO1 mRNA under the hypoxic condition was 1.5-fold higher than that under the normoxic condition. This suggests that cilia formed under the hypoxic condition are longer than those formed under the normoxic condition.

Figure 11A:
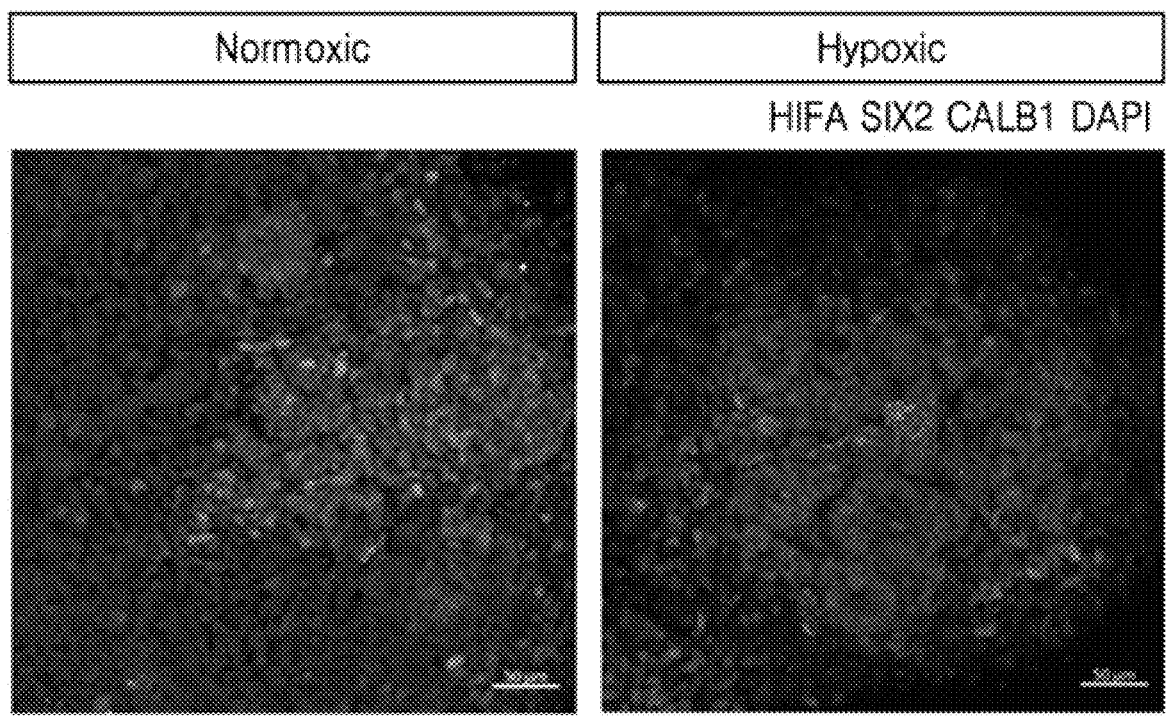
FIGS. 11(a) and 11(b) show the results of observing and comparing the morphology and differentiation pattern of ureteral buds (UB).
Figure 11B:
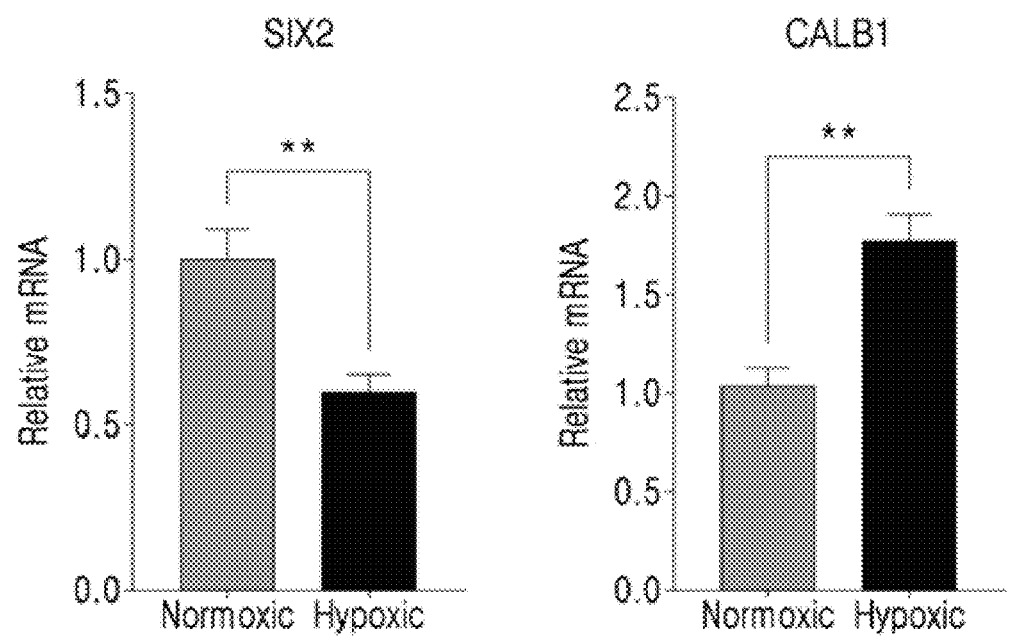

FIGS. 11(a) and 11(b) show the results of observing and comparing the morphology and differentiation pattern of ureteral buds (UB). The period in which nephron stem cells are formed as the collecting ducts are formed is 9 days. As a result of comparing the morphology and differentiation pattern of ureteral buds (UB) between a normoxic condition (21% oxygen concentration) and a hypoxic condition (5% oxygen concentration), it was confirmed that significantly different patterns appeared in both conditions. Referring to FIG. 11(a), it can be confirmed that CALB1, which is used as both a collecting duct marker and a UB marker, was expressed in both conditions, but the expression pattern thereof did not form a specific structure under the normoxic condition, but under the hypoxic condition, CALB1 was structurally expressed along the periphery of the kidney vesicles in which SIX2 was expressed. In addition, as a result of staining and comparing the hypoxia inducer (HIF1A), which is known to accumulate in a hypoxic environment, it was confirmed that the expression level in of HIF1A under the hypoxic condition was significantly higher than that in the normoxic condition, and it could be inferred that HIF1A accumulated in the site where CALB1 was expressed, and had an effect on the development of the collecting duct. Meanwhile, as a result of comparing the expression levels of mRNA in metanephric mesenchyme (MM) cells and UB cells at the gene level, it could be confirmed that the expression level of the MM marker SIX2 was lower under the hypoxic condition than under the normoxic condition, whereas the expression level of the UB marker CALB1 was 1.5-fold higher under the hypoxic condition, suggesting that the collecting duct could be formed under the hypoxic condition due to the development of UB cells during the differentiation process.

Figure 12:
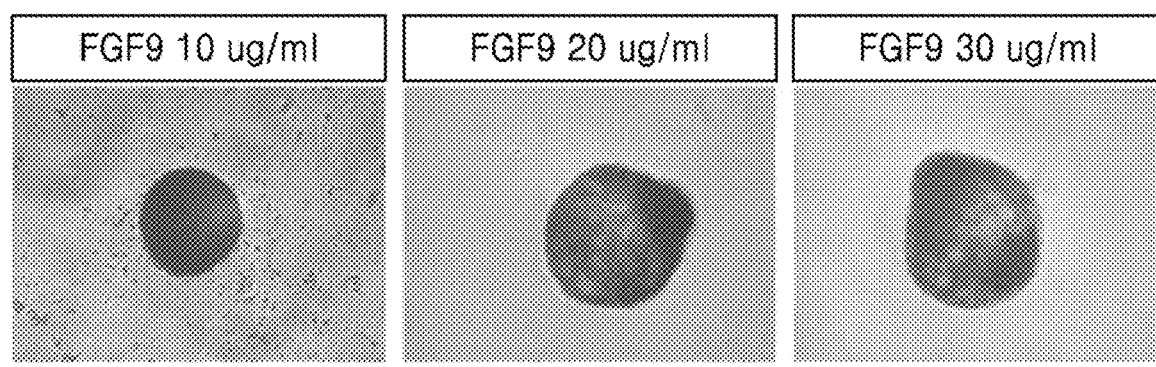
FIG. 12 shows development into a nephron structure depending on the concentration of FGF9 in step (3).

(2) Difference Depending on FGF9 Concentration in Step (3) of Differentiating into Organoids Kidney organoids were produced in the same manner as in Example 1, except that, in step (3), cells were treated with a medium containing FGF9 at a concentration of 10 μg/ml or 20 μg/ml. In this case, there was a problem in that organoids did not stably have a nephron structure for all the media. Meanwhile, it was observed that, when differentiation into kidney organoids was performed using a medium containing FGF9 at a concentration of 30 ng/ml as described in Example 1, cells developed more stably into a nephron structure, and in particular, cells were clearly differentiated into a tubular structure. Therefore, it was confirmed that, in step (3) of differentiating into kidney organoids, cells are preferably treated with FGF9 at a higher concentration of 30 ng/ml. FIG. 12 shows development into a nephron structure depending on the concentration of FGF9 in step (3).

Figure 13:
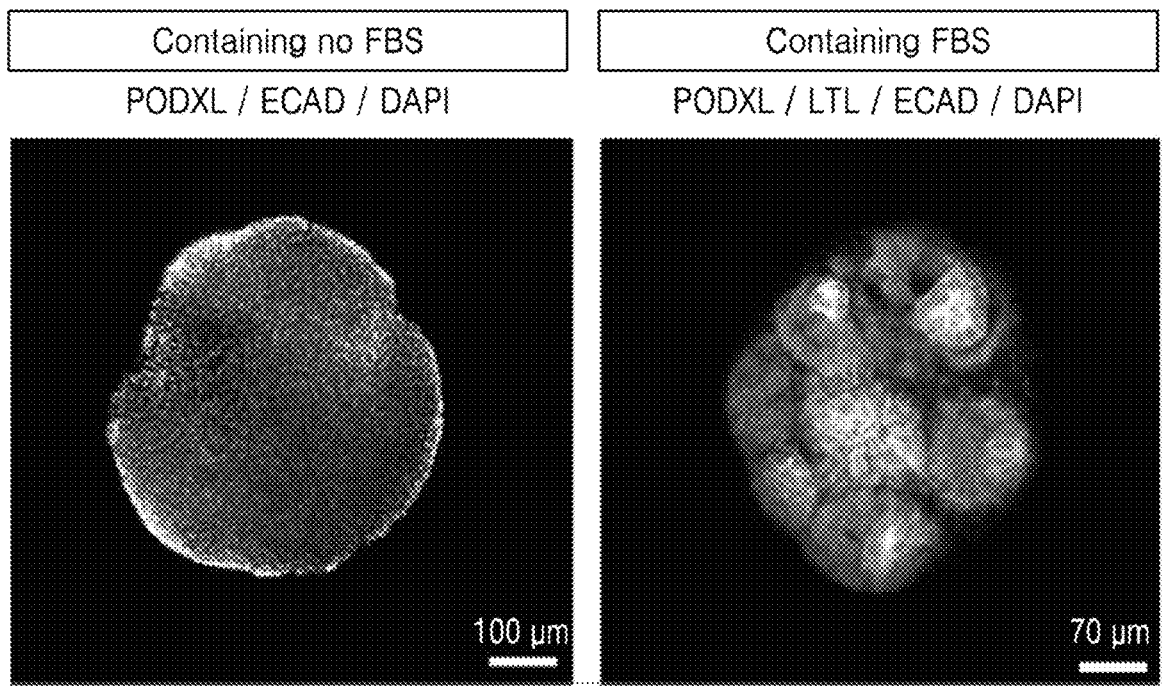
FIG. 13 shows the results of analyzing the degree of differentiation depending on whether or not FBS is included in step (3), by immunofluorescence staining.

(3) Difference Depending on Whether or not Medium Contains FBS in Step (3) of Differentiating into Organoids The degree of differentiation depending on whether FBS was contained in medium in step (3) of differentiating into organoids was analyzed by immunofluorescence staining, and the results are shown in FIG. 13. As shown in FIG. 13, it was confirmed that a nephron structure could not be observed in the kidney organoids differentiated using a medium composition containing no FBS, but kidney organoids differentiated using a medium composition containing FBS in an amount of 1.5 vol % based on the total volume of the medium composition had a nephron-like structure therein.

4. Evaluation of Drug Toxicity of Kidney Organoids

Kidney organoids were treated with advanced RPMI 1640 containing 0, 30 or 60 μM of tacrolimus at 37° C. for 24 hours, and after 24 hours, the kidney organoids were washed 3 times with DPBS. Next, live cells and dead cells were stained with calcein-AM and ethidium homodimer-1, respectively. According to this process, the drug toxicity of the kidney organoids obtained in Example 1 was evaluated.

Figure 14:
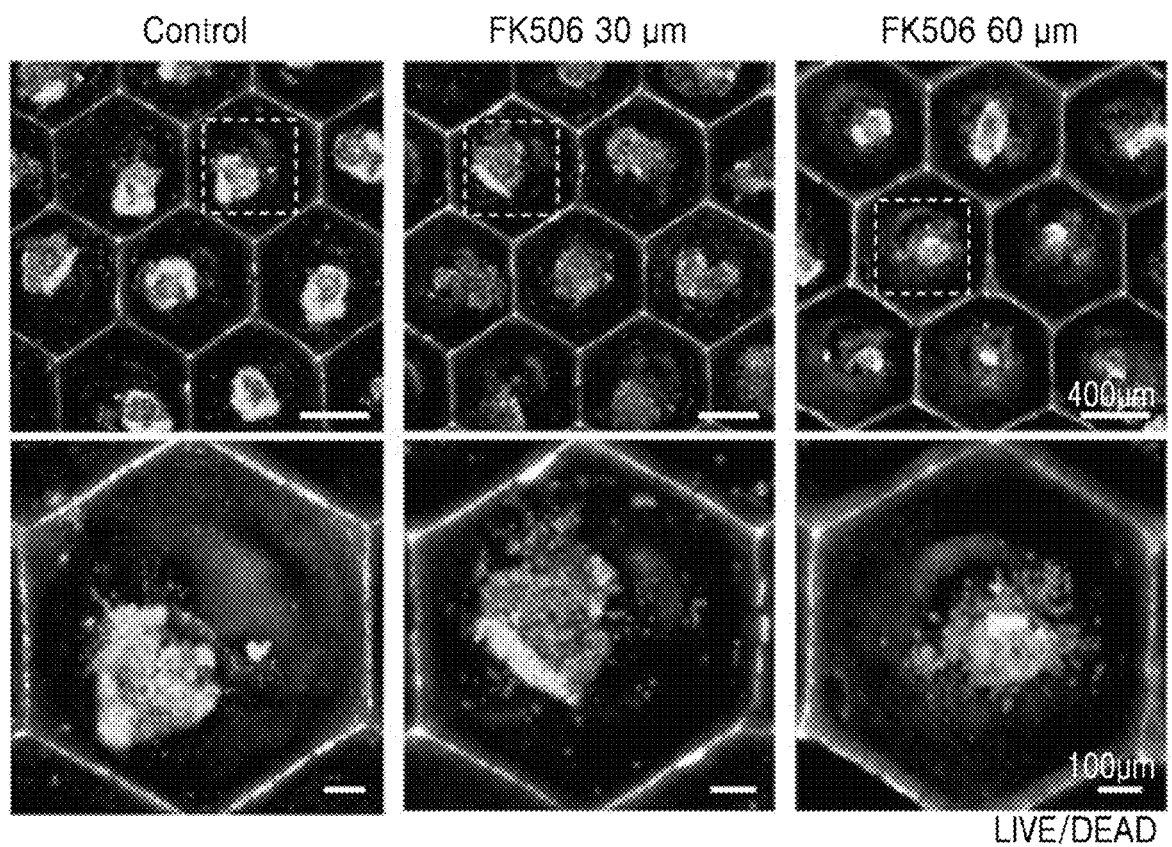
FIG. 14 shows the results of evaluating the drug toxicity of kidney organoids formed on permeable wells in an example of the present disclosure.

As a result, as shown in FIG. 14, it was observed that, when the kidney organoids were treated with various concentrations of tacrolimus (FK506), which is known to be toxic to the kidneys, the number of dead cells increased as the concentration of tacrolimus increased, suggesting that organoids were produced by the present disclosure.

Although the embodiments of the present disclosure have been described in detail, the scope of the present disclosure is not limited thereto, and it will be apparent to those of ordinary skill in the art that various modifications and variations are possible without departing from the technical spirit of the present disclosure as described in the appended claims.

What is claimed is:

1. A method for producing human kidney organoids comprising:
(A) differentiating human pluripotent stem cells into metanephric mesenchyme cells by:
(i) culturing the human pluripotent stem cells in a first medium containing a GSK-3β inhibitor and a BMP4 inhibitor on Day 0,
(ii) culturing the human pluripotent stem cells in a second medium containing Activin A on day 4,
(iii) culturing the human pluripotent stem cells in a third medium containing 10 ng/ml of FGF9 on day 7;
(B) forming metanephric mesenchyme cell aggregates by culturing the metanephric mesenchyme cells in a fourth medium containing a GSK-3p inhibitor and 10 ng/ml of FGF9 on Day 9; and
(C) differentiating the metanephric mesenchyme cell aggregates into kidney organoids in a fifth medium containing FBS on day 14 for 7 to 100 days and culturing the metanephric mesenchyme cells in a sixth medium containing 25 ng/ml to 50 ng/ml of FGF9 on Day 11 to form kidney organoids;

wherein steps (B) and (C) are performed in a porous microwell formed of a permeable porous membrane comprising at least one concave portion, wherein the at least one concave portion is formed at the bottom and an opening is formed at the top of the microwell, wherein the porous microwells facilitate supply of nutrients and growth factors and removal of metabolites.

2. The method according to claim 1, wherein step (A) of differentiating the human pluripotent stem cells into the metanephric mesenchyme cells is performed in a hypoxic environment with an oxygen concentration lower than 10%.

3. The method according to claim 1, wherein step (A) of differentiating the pluripotent stem cells into the metanephric mesenchyme cells is performed for 8 days to 9 days.

4. The method according to claim 1, wherein step (B) of forming the metanephric mesenchyme cell aggregates is performed for 2 days to 3 days.

* * * * *